(12) United States Patent
Sheehan et al.

(10) Patent No.: US 8,066,646 B2
(45) Date of Patent: Nov. 29, 2011

(54) LARGE DIAMETER PLETHYSMOGRAPH

(75) Inventors: Vito Sheehan, Danbury, CT (US); Richard A. Larson, North Warnborough (GB)

(73) Assignee: Buxco Electronics, Inc., Sharon, CT (US)

(*) Notice: Subject to any disclaimer, the term of this patent is extended or adjusted under 35 U.S.C. 154(b) by 1043 days.

(21) Appl. No.: 11/291,190

(22) Filed: Dec. 1, 2005

(65) Prior Publication Data
US 2007/0179394 A1  Aug. 2, 2007

(51) Int. Cl.
*A61B 5/08* (2006.01)

(52) U.S. Cl. .................................................. 600/529

(58) Field of Classification Search .......... 600/529, 600/538
See application file for complete search history.

(56) References Cited

U.S. PATENT DOCUMENTS

| | | | |
|---|---|---|---|
| 3,102,741 A * | 9/1963 | Lash | ................ 285/332.3 |
| 4,479,493 A | 10/1984 | Bung et al. | |
| 4,520,808 A | 6/1985 | LaBauve | |
| H145 H | 10/1986 | James | |
| 4,622,852 A | 11/1986 | James et al. | |
| 4,841,982 A | 6/1989 | Nikiforov et al. | |
| 5,379,777 A | 1/1995 | Lomask | |
| 5,381,729 A * | 1/1995 | Hennessy et al. | ............... 99/483 |
| 6,902,532 B2 * | 6/2005 | Lomask | ....................... 600/529 |
| 2002/0120207 A1 * | 8/2002 | Hoffman | ...................... 600/538 |

* cited by examiner

Primary Examiner — Patricia Mallari
Assistant Examiner — Christian Jang
(74) Attorney, Agent, or Firm — MacCord Mason PLLC

(57) ABSTRACT

A plethysmograph is described that includes a reference chamber having a top wall, a bottom wall, a barrier wall spaced beneath the bottom wall, a continuous side wall having a lower edge, and a first continuous flange with a lower edge below the bottom wall and above the barrier wall; a test chamber having a bottom wall, a continuous side wall with an upper edge, and a second continuous flange extending upwardly from the upper edge, the interior face of one of the flanges including an annular groove with an O-ring in the groove, and the interior face of the other flange being tapered from vertical by up to about 1°; and a manifold having airflow openings in communication with the reference and test chamber and a common exterior airflow opening through a passageway, and a sampling port in communication with the passageway.

21 Claims, 2 Drawing Sheets

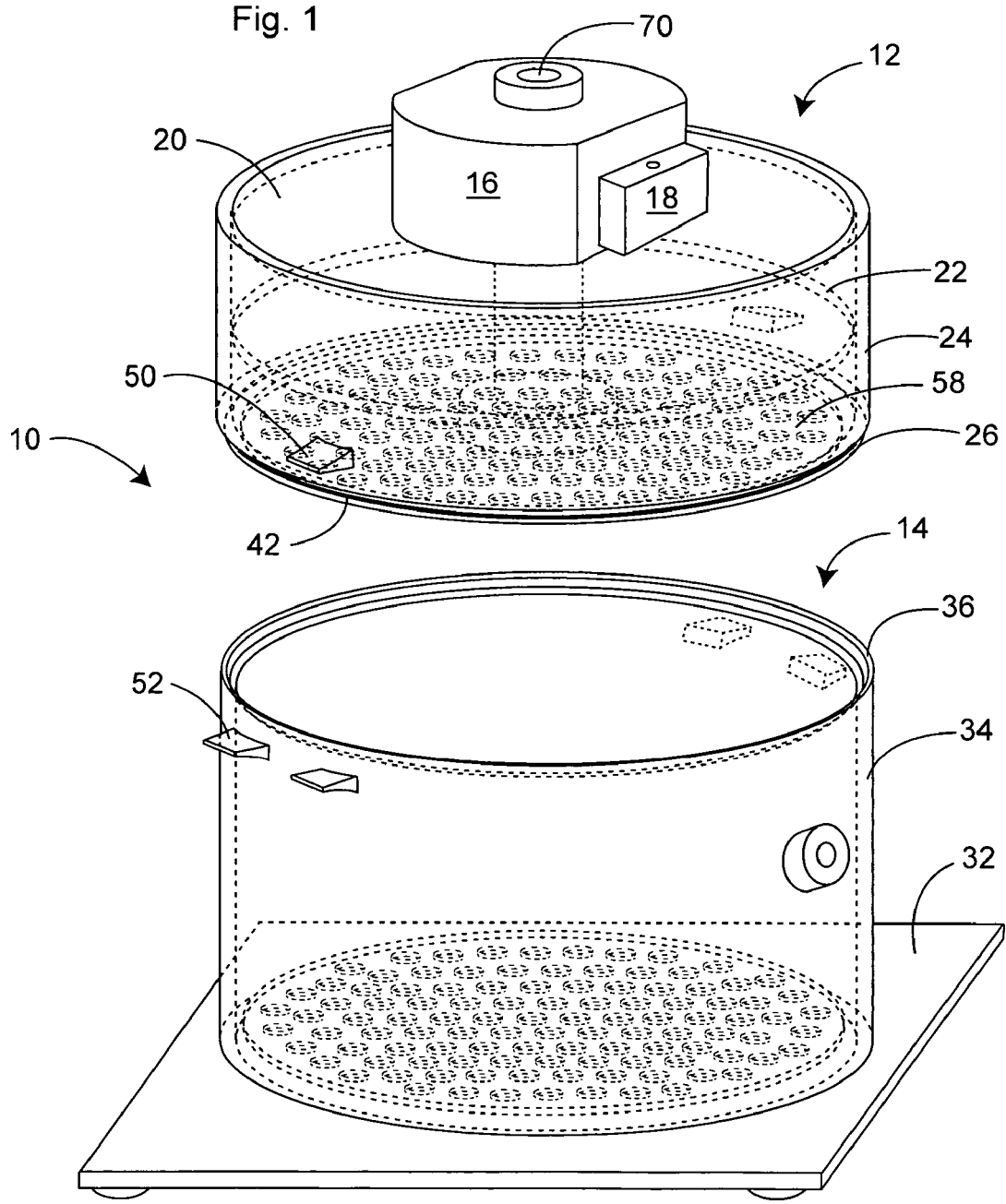

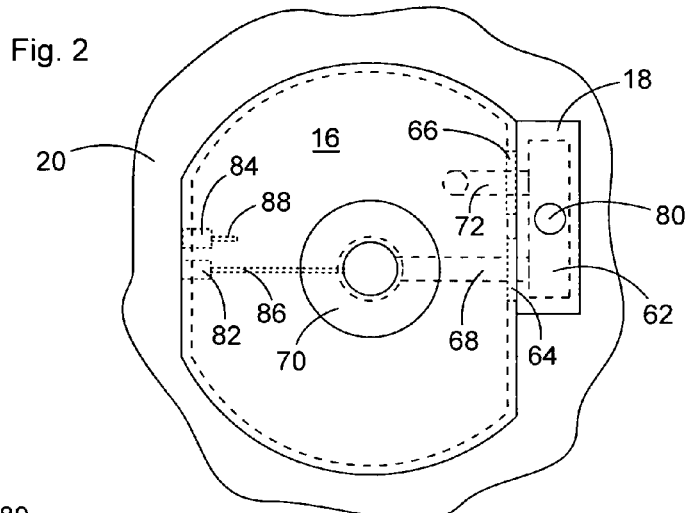
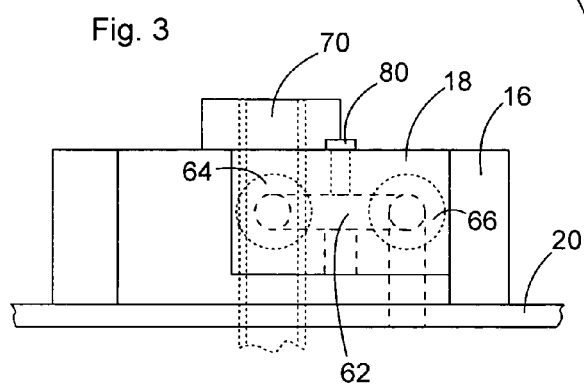
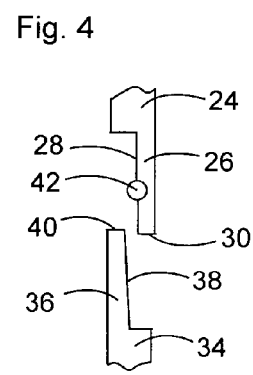
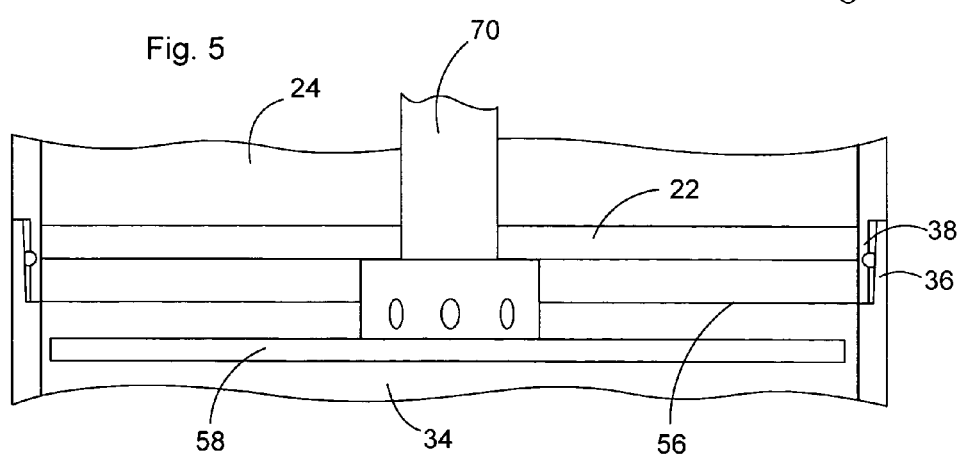

LARGE DIAMETER PLETHYSMOGRAPH

BACKGROUND OF THE INVENTION (1) Field of the Invention

The present invention relates to plethysmographs used to measure changes in air volume, such as in non-invasive pulmonary testing of small animals, and in particular to larger plethysmographs that provide a test chamber with an airtight seal without the use of clamps, but which can be readily opened when desired. The invention further relates to a reduced noise plethysmograph that include means for air sampling.

(2) Description of the Prior Art

Plethysmographs are used in research to collect data relating to changes in air pressure within a test chamber. An example of such data is pulmonary data from small animals, such as mice. Most plethysmographs are comprised of a test chamber to enclose the test subject, a reference chamber, and a differential pressure transducer connected to the two chambers, e.g., via tubing extending from a port in each chamber to the transducer. Both chambers are in communication with the ambient air, i.e., the air within the room where the tests are being conducted, through restricted airflow openings, or pneumotachs.

As changes to the air volume within the test chamber occur, pressure variations are recorded by the transducer, which normally displays the recorded data in numerical form or as a graph. Air pressure within the test chamber can also vary due to changes in the pressure of air entering the test chamber through the pneumotachs. This non-chamber originated air pressure variation, known as background noise or simply noise, can adversely affect the accuracy of the recorded data, since the transducer also measures the noise.

Plethysmographs are commonly used to measure the pulmonary activities of test animals that are completely or substantially enclosed within the test chamber. As the test animal inhales or exhales, the changes in air volume results in pressure variations that are recorded by the transducer.

The purpose of the reference chamber is to partially reduce the noise affect. A second tube extends from a reference chamber outlet to the transducer. The transducer simultaneously measures variations in air pressures within the two chambers, and subtracts the reference chamber measurements from the animal chamber measurements. As a result, the net pressure variations are essentially attributable to the respiration patterns of the test animal. Preferably, the test and reference chamber pneumotachs are close to each other to minimize variations in exterior air patterns.

A representative plethysmograph of the type used to measure small animal pulmonary responses is shown and described in commonly assigned U.S. Pat. No. 5,379,777 to Lomask, the entire disclosure of the patent being incorporated herein by reference.

U.S. Pat. No. 6,902,532 to Lomask, the entire disclosure of this patent also being incorporated herein by reference, describes an apparatus for further reducing background noise. In accordance with the disclosure of the '532 patent, a noise-reduction manifold is provided to direct exterior air from a common opening into both the reference and test chambers. Preferably, the distance from the exterior air opening to the two chambers is approximately the same, so that any changes in air entering the manifold will be equally experienced by both chambers. As a result, subtraction of reference chamber pressures from test chamber pressures provides essentially a noise-free measurement of pressure changes within the test chamber that is attributable to the test subject.

However, further improvements in plethysmographs of the type described in the above patents are still desired, especially in plethysmographs sized to accommodate larger test subjects. In particular, there is a need for a plethysmograph having a reference chamber that is attachable to a test chamber in a manner that will result in an airtight enclosure of the test chamber without the use of latches or clamps, while still enabling the operator to quickly and easily open the test chamber when desired. There is also a need for a reduced noise plethysmograph that includes a means for quickly and accurately sampling the air that is entering the test chamber.

SUMMARY OF THE INVENTION

The present invention is directed to improved plethysmographs, and in particular to larger plethysmographs that provide a test chamber with an airtight seal without the use of clamps, but which can be readily opened when desired. The plethysmograph may also include a noise-reduction manifold that includes means for air sampling.

Generally, the improved plethysmograph is comprised of a reference chamber, a test chamber with an open top adapted to receive the reference chamber to form an airtight seal, and a means, in particular a noise reduction manifold, to provide air to the two chambers. The chambers are preferably constructed of a transparent plastic.

The reference chamber is comprised of a top wall, a bottom wall parallel to and spaced below the top wall, and a continuous side wall extending around the peripheries of the top and bottom walls. Preferably, the top and bottom walls are circular and the side wall is cylindrical. The reference chamber side wall has a lower edge that includes a downwardly extending continuous flange that has an interior face and a lower edge.

The test chamber is comprised of a bottom wall and a continuous side wall extending upwardly from the bottom wall. The side wall has a lower edge joined to the bottom wall and an upper edge that includes an upwardly extending continuous flange that has an interior face and an upper edge. The side walls of the two chambers are preferable cylindrical and of the same diameter.

The flanges are sized to join the reference chamber to the top of the test chamber with the interior faces of the flanges being toward each other. Preferably, the reference chamber flange is the interior flange, while the test chamber flange is the exterior flange. That is, the reference chamber flange fits on the inside of the test chamber flange, with the lower end of the reference chamber flange being adjacent the upper edge of the test chamber side wall and the upper edge of the test chamber flange being adjacent the lower edge of the reference chamber side wall.

In order to ensure an airtight seal between the interior faces of the flanges, an O-ring is positioned within an annular groove in one of the interior faces, e.g., the interior face of the reference chamber flange. As the reference chamber is attached over the test chamber, the adjacent interior faces compress the O-ring to form an airtight seal.

The combination of the flanges and O-ring is highly effective in producing an airtight seal. In fact, the seal can be so effective that opening of the test chamber can be difficult with larger plethysmographs, e.g., when the diameter of the test chamber is greater than about six inches. This difficulty is addressed by the present invention by slightly tapering one of the flange interior faces toward the end of the flange so that the spacing between the flange faces is greater at the end of the tapered flange than at the base of the tapered flange. Therefore, as the chamber is opened the pressure against the O-ring quickly diminishes facilitating opening of the chamber.

Opening of the test chamber is also facilitated by the inclusion of exterior finger tabs that project outward from adjacent the lower edge of the reference chamber side wall and from adjacent the upper edge of the test chamber side wall. These tabs can be used by the operator to lever the chambers apart. Preferably, the reference chamber includes one pair of opposed tabs, while the test chamber includes two pairs of opposed tabs offset by about 20-40°. When attaching the reference chamber to the test chamber, the reference chamber tabs are positioned between the test chamber tabs. The operator can then pull upwardly on one of the reference chamber tabs while pressing downwardly on one or both of the adjacent test chamber tabs to force the chambers apart.

The annular intersection of the chambers is spaced below the bottom wall of the reference chamber and is defined on the interior of the test chamber by the lower edge of the reference chamber flange and the upper end of the test chamber side wall. A small gap may be left between these components to ensure a tight fit of the flange interior faces against the O-ring. To avoid destructive chewing of this intersection by test animals, the plethysmograph also includes a barrier wall spaced below the bottom wall of the reference chamber, so that the intersection is below the bottom wall and above the barrier wall. The barrier wall, which has a cross-sectional area approximating the cross-sectional area of the interior of the test chamber, blocks access of the test animal to the intersection. Preferably, the barrier wall is air permeable, e.g., perforated, so as not to interfere with the flow of aerosols into the test chamber.

The reference and test chambers each include restricted airflow openings to permit air to flow to and from the chambers. The airflow opening may be a pneumotach or pneumotachograph, which is basically a restricted airflow opening that may include a screen covering the opening to create a pressure drop. Preferably, these airflow openings communicate with the exterior of the plethysmograph through a common inlet as described in the '532 patent noted above to reduce background noise resulting from differences in the air pressure to the chambers.

As described in the '532 patent, the chambers may communicate with the exterior through a manifold which includes airflow openings to the chambers and an exterior airflow opening, with passageways connecting the exterior opening to the chamber airflow openings. Preferably, the length of the passageways from the exterior airflow opening to the chamber airflow openings are approximately equal to minimize differences in timing and resultant noise. In the present plethysmograph, the manifold is preferably mounted on the top of the reference chamber. As will be described in detail hereinafter, a mounting block may be secured to the top of the reference chamber with the noise reduction manifold being attached to the mounting block. Passageways then extend through the mounting block from the airflow openings in the manifold to the chambers.

The test chamber may also include a bias-air outlet connected to a vacuum source to draw air through the test chamber to reduce heat and humidity within the chamber and prevent the test animal from rebreathing air. If a test gas or aerosol is to be inserted into the chamber, the test chamber may also include an aerosol inlet or manifold having an inlet connectible to a gas or aerosol source, and an outlet within the test chamber. When the plethysmograph is used in testing small animals, the test chamber may also include a perforated floor spaced above the bottom wall to separate the animal from feces and urine.

The two chambers also include outlets or ports for connecting a differential pressure transducer to the two chambers. For example, the ports may be positioned in the mounting block noted above, with transducer passageways extending through the block from the ports to the chambers. Tubes may then extend from the ports to the transducer. The transducer is in turn connected to a recorder, usually through an amplifier, to record changes in air pressure, indicating changes in air volume. Simultaneous measurement of air changes within the reference chamber permits changes in exterior air pressure to be partially subtracted from the measured values. As a result, the recorded measurements largely reflect actual pressure changes created by the test subject within the test chamber.

BRIEF DESCRIPTION OF THE DRAWINGS

FIG. 1 is a perspective, view of the open plethysmograph.
FIG. 2 is a top view of the mount and noise-reduction manifold.
FIG. 3 is a front view of the mount and noise-reduction manifold.
FIG. 4 is a detail sectional side view of the flanges.
FIG. 5 is a sectional side view of the interface of the reference and test chambers.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

As best illustrated in FIG. 1, a preferred plethysmograph, generally 10, is comprised of a reference chamber, generally 12, an open-top test chamber, generally 14, and mounting block 16 supporting noise reduction manifold 18.

Reference chamber 12 is comprised of a top wall 20, a bottom wall 22, and a continuous side wall 24 extending around the peripheries of top wall 20 and bottom wall 22. The lower edge of side wall 24 extends below bottom wall 22 and includes a downwardly extending continuous flange 26 that has an interior face 28 and a lower edge 30.

Test chamber 14 is comprised of a footed base 32 with an upper surface acting as a bottom wall and a continuous side wall 34 extending upwardly from the bottom wall. Side wall 34 has an upper edge with an upwardly extending continuous flange 36 that has an interior face 38 and an upper edge 40.

Flanges 26 and 36 are sized to join to attach reference chamber 12 onto the top of test chamber 14 with the interior faces 28 and 38 of flanges 26 and 36, respectively, being toward each other. Preferably, reference chamber flange 26 is the interior flange, while test chamber flange 36 is the exterior flange.

In order to ensure an airtight seal between the interior faces of flanges 26 and 36, an O-ring 42 is positioned within an annular groove 44 in one of the flange interior faces, e.g., the interior face of reference chamber flange 26. As reference chamber 12 is attached onto test chamber 14, adjacent interior faces 28 and 38 compress O-ring 42 to form an airtight seal.

In order to facilitate opening of plethysmograph 10, flange face 38 is tapered, preferably by about 1° from vertical so that the spacing between faces 28 and 38 is greater at the end of tapered flange 38 than at its base. Therefore, as the chambers are separated the compression of O-ring 42 quickly diminishes to facilitating opening.

Opening of plethysmograph 10 is also facilitated by the inclusion of exterior finger tabs 50 that project outward from opposite sides of side wall 24 of reference chamber 12 and opposed pairs of finger tabs 52 extending from side wall 34 of test chamber 14. Tabs 50 and 52 are used to lever chamber 12 away from chamber 14 breaking the seal between O-ring 42 and interior face 38.

Interior intersection 56 of chambers 12 and 14, which may be a small gap, is spaced below bottom wall 22 of reference chamber 12. Perforated barrier wall 58, having a cross-sectional area approximating the cross-sectional area of the interior of test chamber 14 is spaced below bottom wall 22 so that intersection 56 is below bottom wall 22 and above barrier wall 58 to block access of the test animal to the intersection.

Noise reduction manifold 18 is mounted on the side of mounting block 16, which in turn is mounted on top wall 20 of reference chamber 12. Manifold 18 includes a T-shaped passageway 62 having a vertical section in communication with an exterior air opening and a horizontal section in communication with pneumotachs 64 and 66. Pneumotach 64 communicates through passageway 68 and aerosol manifold 70 with the interior of test chamber 14, while pneumotach 66 communicates through passageway 72 with reference chamber 12. As a result, noise due to variations in exterior air pressure is avoided.

During animal testing, it is often desirable to withdraw test samples the air within the animal's environment, e.g., for gas concentrations, or temperature and humidity of air exiting or entering the test chamber. Air sampling should ideally be conducted without changing the pressure of the animal's environment. In the present invention, manifold 18 also includes air sampling port 80 located between pneumotach 64 leading to test chamber 14 and the exterior air port. Preferably, port 80 is located adjacent pneumotach 64 so that the air sampled will closely approximate the air within chamber 14 and not the exterior air. In instances where the bias air flow draws air into test chamber 14 through pneumotach 64, sampling port 80 can also be used to sample air entering into chamber 14.

Mounting block 16 also includes pressure transducer ports 82 and 84 for connection of chambers 12 and 14, respectively, to a differential pressure transducer. Port 82 communicates with test chamber 14 through transducer passageway 86 and aerosol manifold 70. Port 84 communicates with reference chamber 12 through transducer passageway 88 in block 16. In a typical arrangement, such as illustrated in the above '532 patent, tubes extend from ports 82 and 84 to a pressure transducer. The transducer is in turn connected to a recorder, usually through an amplifier, to record changes in air pressure, indicating changes in air volume. Simultaneous measurement of air changes within the reference chamber permits changes in exterior air pressure to be partially subtracted from the measured values. As a result, the recorded measurements largely reflect actual pressure changes created by the test subject within the test chamber. Measurements attributable to noise are further reduced by the above noise reduction chamber.

Certain modifications and improvements will occur to those skilled in the art upon a reading of the foregoing description. For example, the flanges may be reversed. The devices may also include other components common to plethysmographs. It should be understood that all such modifications and improvements have been deleted herein for the sake of conciseness and readability but are properly within the scope of the following claims.

What is claimed is:

1. A plethysmograph comprising:
   a) a reference chamber having a first transducer port for connecting said reference chamber to a pressure transducer;
   b) a test chamber having a second transducer port for connecting said test chamber to said pressure transducer; and
   c) a manifold having a first airflow opening in communication with said reference chamber, a second airflow opening in communication with said test chamber, an exterior airflow opening, a passageway connecting said exterior airflow opening to said first and second airflow openings, and an air sampling port in communication with said passageway between said second airflow opening and said exterior airflow opening, whereby air closely approximating the air in the test chamber can be sampled as well as air entering the test chamber.

2. The plethysmograph of claim 1, wherein said passageway is comprised of a first section in communication with said first and second airflow openings and a second section having an inner end in communication with said first section at a juncture between said first and second airflow openings and an outer end forming said exterior airflow opening.

3. The plethysmograph of claim 2, wherein said sampling port is in communication with said passageway at the juncture of said first and second passageway sections.

4. The plethysmograph of claim 2, wherein the juncture of said first and second sections is equidistant from said first and second airflow openings.

5. The plethysmograph of claim 1, wherein a bottom wall of said reference chamber forms a top wall of said test chamber.

6. A plethysmograph comprising:
   a) a reference chamber having a first transducer port for connecting said reference chamber to a pressure transducer, a top wall, a bottom wall, a continuous side wall with a lower edge, and a first continuous flange with a first interior face and a flange lower edge extending downwardly from said side wall lower edge;
   b) a test chamber having a second transducer port for connecting said test chamber to said pressure transducer, a bottom wall and a continuous side wall with an upper edge, a second continuous flange including a second interior face extending upwardly from said upper edge, one of the first and second interior faces including an annular groove with an O-ring in said groove, the other of the first and second interior faces being tapered relative to the one of the first and second interior faces, said flanges being joinable to form an airtight seal with said O-ring being compressed between said flanges, the compression on said O-ring being diminished due to the other of the first and second interior faces being tapered relative to the one of the first and second interior faces as said chambers are separated to facilitate opening; and
   c) a manifold having a first airflow opening in communication with said reference chamber, a second airflow opening in communication with said test chamber, an exterior airflow opening, a passageway connecting said exterior airflow opening to said first and second airflow openings, and a sampling port in communication with said passageway between said second airflow opening and said exterior airflow opening.

7. The plethysmograph of claim 6, further including a footed base with an upper surface, said upper surface forming said bottom wall.

8. The plethysmograph of claim 6, wherein said side walls are cylindrical and of the same diameter.

9. The plethysmograph of claim 6, wherein said first flange is an interior flange and said second flange is an exterior flange.

10. The plethysmograph of claim 6, wherein said test and reference chambers include finger engageable tabs extending outwardly from said side walls, whereby a user can push a reference chamber tab away from a test chamber tab to separate the reference chamber from the test chamber.

11. The plethysmograph of claim 6, wherein one of said flanges is tapered from vertical by up to about 1°.

12. A plethysmograph comprising:
  a) a reference chamber having a top wall, a bottom wall, a barrier wall spaced beneath said bottom wall, a continuous side wall having a lower edge, and a first continuous flange with a first interior face and a flange lower edge extending downwardly from said side wall lower edge, said first flange including an interior face and a flange lower edge below said bottom wall and above said barrier wall; and
  b) a test chamber having a bottom wall and a continuous side wall with a lower edge joined to said bottom wall and a upper edge with an upwardly extending second continuous flange including a second interior face tapered relative to the other flange face, said flanges being joinable to form an airtight seal with said O-ring being compressed between said flanges, the compression on said O-ring being diminished due to the second interior face being tapered relative to the other flange face as said chambers are separated to facilitate opening; and
  c) a manifold having a first airflow opening in communication with said reference chamber, a second airflow opening in communication with said test chamber, an exterior airflow opening, a passageway connecting said exterior airflow opening to said first and second airflow openings, and a sampling port in communication with said passageway between said second airflow opening and said exterior airflow opening.

13. The plethysmograph of claim 12, wherein the interior face of one of said flanges including an annular groove with an O-ring in said groove.

14. The plethysmograph of claim 12, wherein said first flange has a tapered interior face.

15. The plethysmograph of claim 12, wherein said test chamber and reference chamber side walls have the same inner and outer diameters.

16. The plethysmograph of claim 12, wherein said barrier wall is air permeable.

17. A plethysmograph comprising:
  a) a reference chamber having a top wall, a bottom wall, a barrier wall spaced beneath said bottom wall, a continuous side wall having a lower edge, and a first continuous flange extending downwardly from said side wall lower edge, said first flange including an first interior face and a flange lower edge below said bottom wall and above said barrier wall; and
  b) a test chamber having a bottom wall and a continuous side wall with an upper edge, and a second continuous flange including a second interior face extending upwardly from said upper edge, one of the first and second interior faces including an annular groove with an O-ring in said groove, the other of the first and second interior faces being tapered from vertical relative to the one of the first and second interior faces, said flanges being joinable to form an airtight seal with said O-ring being compressed between said flanges, the compression on said O-ring being diminished due to the other of the first and second interior face being tapered from vertical relative to the one of the first and second interior faces as said chambers are separated to facilitate opening; and
  c) a manifold having a first airflow opening in communication with said reference chamber, a second airflow opening in communication with said test chamber, an exterior airflow opening, a passageway connecting said exterior airflow opening to said first and second airflow openings, and a sampling port in communication with said passageway between said second airflow opening and said exterior airflow opening.

18. The plethysmograph of claim 17, wherein said sampling port is in communication with said passageway equidistant from said first and second airflow openings.

19. The plethysmograph of claim 17, wherein said side walls are cylindrical and of the same diameter.

20. The plethysmograph of claim 17, wherein said test and reference chambers include finger engageable tabs extending outwardly from said side walls, whereby a user can push a reference chamber tab away from a test chamber tab to separate the reference chamber from the test chamber.

21. The plethysmograph of claim 17, wherein the interior face of said first flange includes an annular groove with an O-ring in said groove, and the interior face of said second flange is tapered from vertical by up to about 1° relative to the interior face of said first flange.

* * * * *